US012173347B2

(12) United States Patent
Ino et al.

(10) Patent No.: US 12,173,347 B2
(45) Date of Patent: Dec. 24, 2024

(54) TECHNIQUE FOR CONTROLLING MOLECULAR WEIGHT OF PHA COPOLYMER PRODUCED BY HALOBACTERIUM

(71) Applicant: SUMITMO FORESTRY CO., LTD., Tokyo (JP)

(72) Inventors: Kotaro Ino, Tokyo (JP); Kouichi Ohshiman, Tokyo (JP); Tomo Kakitani, Tokyo (JP); Tomotake Morita, Tsukuba (JP); Tokuma Fukuoka, Tsukuba (JP); Shun Sato, Tsukuba (JP); Azusa Saika, Tsukuba (JP); Kazunori Ushimaru, Tsukuba (JP)

(73) Assignee: Sumitomo Forestry Co., LTD., Tokyo (JP)

(*) Notice: Subject to any disclaimer, the term of this patent is extended or adjusted under 35 U.S.C. 154(b) by 884 days.

(21) Appl. No.: 17/276,965

(22) PCT Filed: Sep. 24, 2019

(86) PCT No.: PCT/JP2019/037215
§ 371 (c)(1),
(2) Date: Mar. 17, 2021

(87) PCT Pub. No.: WO2020/066987
PCT Pub. Date: Apr. 2, 2020

(65) Prior Publication Data
US 2022/0033864 A1    Feb. 3, 2022

(30) Foreign Application Priority Data
Sep. 27, 2018 (JP) .................................. 2018-182989

(51) Int. Cl.
*C12P 7/625*    (2022.01)
*B29C 55/00*    (2006.01)
*B29C 55/02*    (2006.01)
*B29K 105/00*   (2006.01)
*C08G 63/06*    (2006.01)
*C08J 5/18*     (2006.01)

(52) U.S. Cl.
CPC ............ *C12P 7/625* (2013.01); *B29C 55/005* (2013.01); *B29C 55/02* (2013.01); *C08G 63/06* (2013.01); *C08J 5/18* (2013.01); *B29K 2105/0085* (2013.01); *C08J 2367/04* (2013.01)

(58) Field of Classification Search
CPC ....... C12P 7/625; B29C 55/005; B29C 55/02; C08G 63/06; C08J 5/18; C08J 2367/04; B29K 2105/0085
See application file for complete search history.

(56) References Cited

U.S. PATENT DOCUMENTS

| | | | | |
|---|---|---|---|---|
| 5,977,291 | A * | 11/1999 | Cox ..................... | C12P 7/625 528/194 |
| 9,175,317 | B2 * | 11/2015 | Sato ..................... | C12N 15/74 |
| 10,233,468 | B2 * | 3/2019 | Arikawa ................ | C12N 9/18 |
| 11,268,113 | B2 * | 3/2022 | Aoki ..................... | C12P 7/62 |
| 2003/0208028 | A1 | 11/2003 | Yano et al. | |
| 2011/0104767 | A1 | 5/2011 | Kawata et al. | |
| 2014/0057326 | A1 | 2/2014 | Sato et al. | |
| 2016/0237462 | A1 | 8/2016 | Arikawa et al. | |
| 2020/0255589 | A1 | 8/2020 | Maehara | |

FOREIGN PATENT DOCUMENTS

| | | | | |
|---|---|---|---|---|
| EP | 2669365 | A1 * | 12/2013 | ............. C12N 15/74 |
| JP | H06145311 | A | 5/1994 | |
| JP | H07303490 | A | 11/1995 | |
| JP | 2003-311824 | A * | 6/2003 | ............. B29C 55/02 |
| JP | 2003319792 | A | 11/2003 | |
| JP | 2004059789 | A | 2/2004 | |
| JP | 37774746 | B2 | 5/2006 | |
| JP | 2011-050337 | A * | 3/2011 | ............... C12P 7/62 |
| WO | 2009/041531 | A1 | 4/2009 | |
| WO | 2012/102371 | A1 | 8/2012 | |
| WO | 2014/065253 | A1 | 5/2014 | |
| WO | 2019/044836 | A1 | 3/2019 | |

OTHER PUBLICATIONS

Ferre-Guell et al., "Biosynthesis and Characterization of Polyhydroxyalkanoates with Controlled Composition and Microstructure", Biomacromolecules (2018) 19:996-1005.

Han et al., "Molecular Characterization of the phaECHm Genes, Required for Biosynthesis of Poly(3-Hdroxybutyrate) in the Extremely Halophilic Archaeon Haloarcula marismortui", Applied and Environmental Microbiology (2007) 73(19):6058-6065.

Han et al., "Biosynthesis, Characterization, and Hemostasis Potential of Tailor-Made Polyy(3-hydroxybutyrate-co-3-hydroxyvalerate) Produced by Haloferax mediterranei", Biomacromolecules (2015) 16:578-588.

Hyakutake et al., "Carboxy-terminal modification of polyhydroxyalkanoate (PHA) via alcoholysis reaction catalyzed by Class IV PHA synthase", Polymer Degradation and Stability (2015) 117:90-96.

Iwata et al., "Mechanical properties of uniaxially cold-drawn films of poly([R]-3-hydroxybutyrate)", Polymer Degradation and Stability (2003) 79:217-224.

Iwata et al., "Mechanical Properties of Uniaxially Cold-Drawn Films of Poly[(R)-3-hydroxybutyrate] and Its Copolymers", Macromol. Symp. (2005) 224:11-19.

(Continued)

*Primary Examiner* — Ganapathirama Raghu
(74) *Attorney, Agent, or Firm* — RAPHAEL BELLUM PLLC (57) ABSTRACT

The purpose of the present invention is to provide a PHA, in particular PHBV, having a molecular weight exceeding 3,610,000 and/or a method for producing such a PHA while controlling the molecular weight thereof. Provided is a copolymer of random copolymerization of 3-hydroxybutanoic acid and 3-hydroxyvaleric acid, having a weight-average molecular weight exceeding 3,610,000.

10 Claims, 1 Drawing Sheet

(56) References Cited

OTHER PUBLICATIONS

Koller et al., "Biosynthesis of High Quality Polyhydroxyalkanoate Co- and Terpolyesters for Potential Medical Application by the Archaeon Haloferax mediterranei", Macromol. Symp. (2007) 253:33-39.

Koller et al., "Potential of Various Archae- and Eubacterial Strains as Industrial Polyhydroxyalkanoate Producers from Whey", Macromol. Biosci. (2007) 7:218-226.

Kusaka et al., "Microbial Synthesis and Physical Properties of Ultra-High-Molecular-Weight Poly[(R)-3-Hydroxybutyrate]", J.M.S. Pure Appl. Chem. (1998) A35(2):319-335.

Lillo et al., "Effects of Culture Conditions on Poly(Beta-Hydroxybutyric Acid) Production by Haloferax mediterranei", Applied and Environmental Microbiology (1990) 56(8):2517-2521.

\* cited by examiner

TECHNIQUE FOR CONTROLLING MOLECULAR WEIGHT OF PHA COPOLYMER PRODUCED BY HALOBACTERIUM

TECHNICAL FIELD

The present invention relates to a technique for controlling a molecular weight of a PHA copolymer produced by a halophilic bacterium, and relates to a method for producing the PHA copolymer under control of a molecular weight thereof by using the halophilic bacterium. Moreover, the present invention also relates to a method for producing the PHA copolymer under control of a molecular weight thereof, and a novel PHA.

BACKGROUND ART

In the latter half of the 20th century, the technology for producing plastics from petroleum developed rapidly, and the spread of plastics drastically changed people's lives. Numerous Nobel Prizes for plastics (nylon by Carothers, polyethylene, polypropylene by Ziegler-Natta, etc.) also are awarded.

In recent years, 10.75 million tons of plastics have been produced annually in Japan alone (2016). On the other hand, most plastics are made from petroleum, causing problems such as the impact of carbon dioxide emissions at the disposal on global warming and the stable supply of petroleum resources. Furthermore, since ordinary plastics are not decomposed in nature once they are released into the environment, the problem of microplastics has been exacerbated by the plastics floating in the sea as they are.

The solutions to such problems include biomass plastics and biodegradable plastics. Biomass plastics are plastics made from raw materials that are not fossil fuel but biomass such as squeezed wastes of corns, sugarcanes, and the like, and wood; biodegradable plastics are plastics which are decomposed into water and carbon dioxide by the function of microorganisms in the environment after use.

Polyhydroxy alkanoic acids (PHAs) are plastics stored as energy storage substances when certain microorganisms are fed with biomass as carbon sources (nutrients) such as sugars and vegetable oils, and they are bioplastics that biodegrade in the environment after use, reducing the environmental load.

Poly(3-hydroxybutanoic acid) (may be referred to as "P(3HB)") was the first discovered PHA, but poly(3-hydroxybutanoic acid) has hard and brittle properties. Further, poly(3-hydroxybutanoic acid) is thermally decomposed in the vicinity of the melting point, so that the temperature range for melt processing is narrow, and it has been considered difficult to apply it for practical use.

However, recently, there have been many reports on improvement of the physical properties by formation of copolymer PHAs and ultrahigh molecular weight PHAs as solutions for these problems. The copolymers with improved physical properties are PHAs into which the second component such as 3-hydroxyvaleric acid (may be referred to as "3HV"), 3-hydroxyhexanoic acid (may be referred to as "3HH") or 4-hydroxybutanoic acid (may be referred to as "4HB") is incorporated as monomer component in addition to 3-hydroxybutanoic acid (may be referred to as "3HB"). Since the introduction of the second component softens the PHAs and lowers the melting points, the introduction of the second component has an advantage of widening a temperature range in melt processing. Further, physical properties are known to be changed greatly depending on an amount of the second component in a PHA; as indicated by the fact that, for example, at 8.2 mol % of 3HV, the melting point is 141° C. and at 25.9% of 3HV, the melting point is 108.4° C. (Non Patent Document 6: Biomacromolecules, 2018, 19, 996), it is known that thermophysical properties can be controlled by molar fractions.

Ultrahigh molecular weight PHAs are PHAs having a weight-average molecular weight of 3 million or more, whereas common PHAs have that of about 300,000 to 1,000,000, and are known to exhibit an improvement in important physical properties (for example, tensile strength and the like) after mold processing as compared with PHAs having normal molecular weights. On the other hand, however, due to the very high molecular weight, the ultrahigh molecular weight PHAs have a problem of high melt viscosity, poorer moldability, and higher cost. Therefore, it is very important to control the molecular weight of the ultrahigh molecular weight PHAs considering the required physical properties and cost.

Regarding a PHA produced by a microorganism and the microorganism producing the PHA, Patent Documents 1 and 2, for example, report a microorganism as high-molecular-weight PHA-producing microorganism, producing a PHBH (3-hydroxybutanoic acid-co-3-hydroxyhexanoic acid polymer) having a molecular weight of more than 4 million.

Patent Document 3 discloses, as a method for controlling a molecular weight of a special PHA comprising residues having a phenyl structure, a thiophene structure, or a cyclohexyl structure in side chains, a molecular weight control technique for a PHA, characterized by adding a special carboxylic acid. Patent Document 4 discloses that, when taking out a PHA after culturing with highly halophilic bacteria, bacterial cells are lysed to solely recover the polyester by washing with water.

Papers on PHAs produced by microorganisms and the microorganisms have also been published, and for example, Non Patent Document 1 discloses glucose as a carbon source as well as culture conditions for allowing a microorganism to produce a PHA and the microorganism used there.

Non Patent Document 2 discloses that a carbon source for producing a PHA by a microorganism is whey sugars (whey), and that in the case of the produced PHA being a PHBV (3-hydroxybutanoic acid-co-3-hydroxyvaleric acid polymer), the polymer had a weight-average molecular weight of 1.05 million, a 3HV fraction of 6%, and the like. Moreover, Non Patent Document 3 discloses that, when a PHBV was produced by a microorganism using whey sugars as a carbon source, the obtained PHBV had a molecular weight of 696,000, a 3HV fraction of 8 to 10%, and the like.

Non Patent Document 4 states that, when a PHA was produced by using acetic acid and propionic acid as carbon sources with nitrogen-fixing bacteria, the PHA had a molecular weight of 3.27 million, a 3HV fraction of 8.2%, and the like.

Non Patent Document 5 states that, when a strain obtained by modifying *Haloferax mediterranei* ATCC 33500 by genetic recombination is used and valeric acid is added to glucose as a carbon source, a 3HV fraction increases, a weight-average molecular weight is from 980,000 to 2 million and the 3HV fraction has a value from 8.9% to 60.3%.

Non Patent Document 6 discloses that, by using *Haloferax mediterranei* DSM1411 and changing the number of carbon atoms of a carboxylic acid as a carbon source from 2 to 11, the molecular weight of the PHBV obtained can be controlled from 460,000 to 3.61 million and the 3HV fraction can be controlled from 0 to 99.5%.

Non Patent Document 7 discloses that, for the culturing of *Escherichia coli* transfected with a PHA-producing gene, addition of alcohol reduces its molecular weight. Non Patent Document 8 states that a P(3HB) having a molecular weight more than 11 million was produced by using a recombinant *Escherichia coli*.

Patent Document 5 as well as Non Patent Documents 9 and 10 describes the strength of the PHAs.

PRIOR ART DOCUMENTS

Patent Document

Patent Document 1: WO2012/102371
Patent Document 2: WO2014/065253
Patent Document 3: JP 2003-319792 A
Patent Document 4: JP 07-303490 A
Patent Document 5: JP 3774746

Non Patent Document

Non Patent Document 1: Applied and environmental microbiology, 1990, 56, 8, 2517
Non Patent Document 2: Macromolecular Symposia 2007, 253, 33
Non Patent Document 3: Macromolecular Bioscience 2007, 7, 218
Non Patent Document 4: Applied and environmental microbiology, 2007, 73, 19, 6058
Non Patent Document 5: Biomacromolecules, 2015, 16, 578
Non Patent Document 6: Biomacromolecules, 2018, 19, 996
Non Patent Document 7: Polymer Degradation and stability 2015, 117, 90
Non Patent Document 8: Journal of Macromolecular Science, Part A Pure and Applied Chemistry, 1998, 2, 35, 319
Non Patent Document 9: Polymer Degradation and Stability 79, 2003, 217-224
Non Patent Document 10: Macromol. Symp. 2005, 224, 11-19

SUMMARY OF INVENTION

Technical Problem

The maximum weight-average molecular weight of PHBVs produced to date is 3.61 million, and a PHBV with a molecular weight exceeding 3.61 million has yet to be obtained. The molecular weight is an important index that affects physical properties and cost of the PHBV.

It hence is an object of the present invention to provide a PHBV having a molecular weight exceeding 3.61 million, and/or to provide a method for producing a PHA comprising the PHBV under control of a molecular weight if necessary.

Solution to Problem

The present inventors have found, as a result of diligent efforts to solve the above problems, that it may be possible to control a molecular weight of a PHA obtained by modifying a carbon source, and as a result of further efforts, have completed the present invention.

More specifically, the present invention relates to at least the following inventions:

[1]

A copolymer of random copolymerization of 3-hydroxybutanoic acid and 3-hydroxyvaleric acid, having a weight-average molecular weight of more than 3.61 million.

[2]

The copolymer according to the above [1], wherein a molar percentage of 3-hydroxyvaleric acid (3HV fraction) to total moles of 3-hydroxybutanoic acid and 3-hydroxyvaleric acid constituting the copolymer is 5.0% to 40.0%.

[3]

A production method for a polyhydroxy alkanoic acid comprising culturing a microorganism to obtain the polyhydroxy alkanoic acid as a culture product,
wherein a carbon source for the culturing comprises a sugar, said sugar is:
(a) glucose and/or a derivative thereof alone,
(b) glucose and a derivative thereof as well as one or more of xylose, cellobiose, glucuronic acid, arabinose, mannose, galactose, sucrose, and derivatives thereof, or
(c) one or more of xylose, cellobiose, glucuronic acid, arabinose, mannose, galactose, sucrose, and the derivatives thereof,
to obtain the polyhydroxy alkanoic acid having a weight-average molecular weight of 1 million or more.

[4]

The production method according to the above [3], wherein one or more of xylose, cellobiose, glucuronic acid, arabinose, mannose, galactose, sucrose, and derivatives thereof in (b) or (c) are xylose and/or cellobiose.

[5]

The production method according to the above [3] or [4], wherein the microorganism is a highly halophilic bacterium.

[6]

The production method according to [5], wherein the highly halophilic bacterium is *Haloferax mediterranei*.

[7]

The production method according to any one of the above [3] to [6], wherein the polyhydroxy alkanoic acid has a weight-average molecular weight is more than 3.61 million.

[8]

The production method according to any one of the above [3] to [7], wherein the polyhydroxy alkanoic acid obtained has a weight-average molecular weight of 6 million or less.

[9]

The production method according to any one of the above [3] to [8], wherein the polyhydroxy alkanoic acid is a copolymer of random copolymerization of 3-hydroxybutanoic acid and 3-hydroxyvaleric acid.

[10]

A method for culturing a microorganism and controlling a molecular weight of a polyhydroxy alkanoic acid obtained as a culture product,
wherein a carbon source for the culturing comprises a sugar, said sugar is:
(a) glucose and/or a derivative thereof alone,
(b) glucose and a derivative thereof as well as one or more of xylose, cellobiose, glucuronic acid, arabinose, mannose, galactose, sucrose, and derivatives thereof, or
(c) one or more of xylose, cellobiose, glucuronic acid, arabinose, mannose, galactose, sucrose, and the derivatives thereof,
to control a weight-average molecular weight of the polyhydroxy alkanoic acid produced between 1 million and 6 million.

[11]
The method according to the above [10], wherein the polyhydroxy alkanoic acid is a copolymer formed by random copolymerization of 3-hydroxybutanoic acid and 3-hydroxyvaleric acid.

[12]
A production method for a polyhydroxy alkanoic acid comprising culturing a microorganism to obtain the polyhydroxy alkanoic acid as a culture product,
wherein a carbon source for the culturing comprises a furfural compound together with a sugar, wherein said sugar is:
(a) glucose and/or a derivative thereof alone,
(b) glucose and a derivative thereof as well as one or more of xylose, cellobiose, glucuronic acid, arabinose, mannose, galactose, sucrose, and derivatives thereof, or
(c) one or more of xylose, cellobiose, glucuronic acid, arabinose, mannose, galactose, sucrose, and the derivatives thereof,
to obtain the polyhydroxy alkanoic acid.

[13]
The production method according to the above [12], wherein the polyhydroxy alkanoic acid has a molecular weight of from 200,000 to 6 million.

[14]
The production method according to the above [12] or [13], wherein the furfural compound is furfural and/or 5-hydroxymethylfurfural or a derivative thereof.

[15]
The production method according to any one of the above [12] to [14], wherein the polyhydroxy alkanoic acid is a copolymer formed by random copolymerization of 3-hydroxybutanoic acid and 3-hydroxyvaleric acid.

[16]
A method for culturing a microorganism and controlling a molecular weight of a polyhydroxy alkanoic acid obtained as a culture product,
wherein a carbon source for the culturing comprises a furfural compound together with a sugar, wherein said sugar is:
(a) glucose and/or a derivative thereof alone,
(b) glucose and a derivative thereof as well as one or more of xylose, cellobiose, glucuronic acid, arabinose, mannose, galactose, sucrose, and derivatives thereof, or
(c) one or more of xylose, cellobiose, glucuronic acid, arabinose, mannose, galactose, sucrose, and the derivatives thereof,
to control a weight-average molecular weight of the polyhydroxy alkanoic acid produced.

[17]
The method according to [16] above, wherein the polyhydroxy alkanoic acid has a molecular weight of from 200,000 to 6 million.

[18]
The method according to [16] or [17] above, wherein the furfural compound is furfural and/or 5-hydroxymethylfurfural or a derivative thereof.

[19]
The method according to any one of the above [16] to [18], wherein the polyhydroxy alkanoic acid is a copolymer of random copolymerization of 3-hydroxybutanoic acid and 3-hydroxyvaleric acid.

[20]
A cold-drawn film of a copolymer of random copolymerization of 3-hydroxybutanoic acid and 3-hydroxyvaleric acid, having a weight-average molecular weight of more than 3.61 million.

[21]
The cold-drawn film according to the above [20], wherein cold drawing comprises the following steps:
(1) melting a copolymer formed by random copolymerization of 3-hydroxybutanoic acid and 3-hydroxyvaleric acid to obtain a molten film,
(2) rapidly cooling the molten film obtained in (1) in ice water to make an amorphous film,
(3) drawing the amorphous film obtained in (2) as it is in ice water to a 10-fold length to orient the amorphous film, and
(4) subjecting the oriented film obtained in (3) to tension heat treatment to obtain a crystallized cold-drawn film.

[22]
The film according to the above [20] or [21], wherein the copolymer of random copolymerization of 3-hydroxybutanoic acid and 3-hydroxyvaleric acid has a 3HV fraction of 5% to 15%.

Advantageous Effects of Invention

The present inventors have found that the aforementioned problems can be solved by utilizing a specific saccharide (the word such as "a sugar", "sugar content" or "sugars" may be used to express synonyms) as a carbon source, and by further appropriately selecting the type of saccharide depending on physical properties required.

With the present invention, by comprising a specific saccharide as a carbon source, a PHBV as an ultrahigh molecular weight copolymer, having a weight-average molecular weight of more than 3.61 million and capable of exceeding 5 million, is provided. Such a PHA can be applied for applications such as reinforcing materials and ultrahigh strength fibers, to which the conventional molecular weights were not applicable.

As PHAs, a PHBH having a molecular weight of more than 4 million (Non Patent Document 1) and a P(3HB) having a molecular weight of more than 10 million (Non Patent Document 8), have been known. A known molecular weight of PHBV, however, is at most 3.61 million: No PHBV having a molecular weight exceeding 3.61 million has been known to date.

On the other hand, with the present invention, a PHBV having a molecular weight greater than 3.61 million is provided.

With the production method of the present invention, a molecular weight of PHA can be controlled to an appropriate molecular weight of, for example, 1 million to 6 million, depending on the physical properties or cost required for the PHA.

Of the production methods of the present invention, the production method further comprising adding a furfural compound as a carbon source enables to control a molecular weight of PHA to a wider range of molecular weights. With the production method of the present invention further comprising adding the furfural compound, a molecular weight of the obtained PHA can be controlled more easily to obtain a desired amount of PHA. In other words, in the production method of the present invention further comprising adding the furfural compound, a change in an amount of PHA produced caused by the addition is small.

With the production method of the present invention, by appropriately selecting the type of a saccharide as a raw material and a carbon source, not only a molecular weight of PHA but also a molar fraction of a second component can be controlled.

Moreover, with the production method of the present invention, since a saccharide of neutral and highly water-soluble is used as a carbon source for controlling a molecular weight, it is not necessary to neutralize a culture solution and is possible to culture it in a high density. When a microorganism is cultured with a carboxylic acid, the culture solution becomes acidic when cultured at a high concentration, which may corrode a manufacturing plant, and has a problem of incapable of growing the microorganism under the acidic condition. In order to solve this problem, it is necessary to neutralize the culture solution, but an operation for that purpose is troublesome and a large amount of bases such as sodium hydroxide is necessarily used, which procedure is industrially unable to be adopted. The production method of the present invention also achieves an effect that successful production of PHA is carried out without bringing about problems accompanying the use of such a carboxylic acid.

Of the production methods of the present invention, with the method using a highly halophilic bacterium (may be referred to as "Haloarchaea"), a PHA can be produced and recovered at a low cost.

It has been known that there are some microorganisms producing a PHA among the types called highly halophilic bacteria that live only in a high-concentration sodium chloride aqueous solution. It has been known that bacterial cells that produce a PHA in the high-concentration sodium chloride aqueous solution are lysed in a low-concentration sodium chloride aqueous solution or in water after production, and the PHA stored in the cells can be taken out (Patent Document 4). Normally, a large amount of organic solvent, surfactant, or the like is used when a PHA is recovered from bacterial cells, but in the case of the highly halophilic bacteria, it can be recovered only with water, which is a great cost advantage.

As a prior art for controlling a molecular weight of PHA in a production thereof with the highly halophilic bacteria, for example, Anna Ferre-Guell et al. have provided a method for producing an ultrahigh molecular weight polymer with *Haloferax mediterranei* using a carboxylic acid as a carbon source, and have further announced a method for producing a PHBV having wide molecular weights between 460,000 and 3.61 million (Non Patent Document 6). In this method, acetic acid, propionic acid, butyric acid, valeric acid, and caproic acid are used as carbon sources when controlling a molecular weight.

Non Patent Document 1 reports that glucose was used as a carbon source and PHA was produced by *Haloferax mediterranei*. However, this document does not disclose PHBV as PHA, nor does it describe molecular weight of PHAs.

Patent Document 1 states that a PHBH having a molecular weight exceeding 4 million was produced by using a specific microorganism. However, what is described in the document is limited to a method for synthesizing a high molecular weight PHA, and the document does not describe acquisition of a high molecular weight PHA while controlling the molecular weight, and a method therefor.

In the production method of the present invention, it is an excellent effect that cannot be predicted from the prior art, to enable to obtain the PHA while controlling a molecular weight of PHA over a wide range thereof.

DESCRIPTION OF EMBODIMENTS

The present invention will be described hereinbelow in more detail. As used herein, unless otherwise stated, a molecular weight of PHA refers to a numerical value measured by gel permeation chromatography using a polystyrene standard.

With the present invention, a novel PHA copolymer having a weight-average molecular weight of more than 3.61 million, wherein 3-hydroxybutanoic acid and 3-hydroxyvaleric acid are randomly copolymerized, is provided, and further, a method for producing a PHA comprising the copolymer is provided.

The production method of the present invention for producing a PHA, can control a molecular weight of the produced PHA and also control a molar fraction of a second component. Such control in the production method of the present invention could be explained as follows: Among sugars used as carbon sources, i.e., glucose or a derivative thereof as well as xylose, cellobiose, glucuronic acid, arabinose, mannose, galactose, sucrose, and derivatives thereof, a consumption rate of glucose or the derivative thereof in microorganisms (in particular, highly halophilic bacteria) is the highest, and a consumption rate of xylose, cellobiose, glucuronic acid, arabinose, mannose, galactose or sucrose, or derivatives thereof, is smaller than the consumption rate of glucose or the derivative thereof; said control hence could be based on adjusting a consumption rate of the entire carbon source supplied by utilizing a difference in the consumption rate of each of these sugars. The principles of the present invention are not bound by such a theory.

As used herein, "to" refers to a numerical range (including two numerical values connected by the "to") specified by a range between the two numerical values. For example, the description "200,000 to 6 million" refers to a range composed of all numerical values existing between 200,000 and 6 million, including 200,000 and 6 million. In order to express the same meaning, the notation "200,000 or more and 6 million or less" may be used.

When a molecular weight of a polymer is numerically expressed in the present description, an intended numerical value is specific values including a range of numerical values understood by a person skilled in the art.

1. Method for Producing PHA

One of the production methods of the present invention for producing a PHA (hereinafter, may be referred to as "the production method of the present invention"), enables to produce a PHA having a weight-average molecular weight of more than 3.61 million, and is described as follows:

A method for producing a polyhydroxy alkanoic acid comprising culturing a microorganism to obtain the polyhydroxy alkanoic acid as a culture product, wherein a carbon source for the culturing comprises a sugar or sugars selected from:

(a) glucose and/or a derivative thereof alone, (b) glucose and the derivative thereof as well as one or more of xylose, cellobiose, glucuronic acid, arabinose, mannose, galactose, sucrose, and derivative thereof, or (c) one or more of xylose, cellobiose, glucuronic acid, arabinose, mannose, galactose, sucrose, and the derivatives thereof, to obtain the polyhydroxy alkanoic acid having a weight-average molecular weight of 1 million or more.

The sugars do not include sugars contained in other nutrient source such as a yeast extract. The sugars refer to those supplied separately from other nutrient source such as a yeast extract.

The sugars used in the production method of the present invention also include a derivative of each of the above sugars. As the derivative of the sugar, an etherified or esterified sugar described above is supposed. In particular, the etherified derivative that is a methoxylated derivative, and the esterified derivative that is an acetylated derivative, are each exemplified.

In the production method of the present invention, the carbon source is not limited as long as it comprises the sugars described in any of the above (a) to (c), and other carbon sources may be contained provided that they contain the sugars described in any of the above (a) to (c). For example, when a sugar derived from a natural product is used, a carbon source other than the sugars described in any of the above (a) to (c) may be present together with the sugars described in any of the above (a) to (c). A preferable production method of the present invention is a method using any of the sugars defined in the above (a) to (c) alone as a carbon source for culturing a microorganism.

As described above, the production method of the present invention can control a molecular weight of the PHA produced and also control a molar fraction of the second component. A plausible principle for the possible control in the production method of the present invention, is as described above (the principle is based on that the consumption rate of the entire carbon source supplied is adjusted by utilizing the difference in the consumption rate of each sugars used for the microorganism as a carbon source).

In the production method of the present invention, a PHA can be produced by controlling a molecular weight of PHA to a weight-average molecular weight of 1 million to 6 million, for example, and by further adding a furfural compound as a carbon source, a PHA having a lower molecular weight can be obtained, and a PHA having a wider range of molecular weights can be produced. In the production method of the present invention adding the furfural compound as a further carbon source, a molecular weight of the PHA produced is not limited; a PHA can be produced by controlling a molecular weight thereof to a weight-average molecular weight of 200,000 to 6 million, for example. The method of the present invention wherein a furfural compound is used will be further described below.

A preferable production method of the present invention is a method of producing a PHA wherein a molecular weight of PHA is controlled to a weight-average molecular weight of 1 million to 5.75 million.

<Carbon Source>

As the above carbon source in the production method of the present invention, (a) if glucose and/or a derivative thereof alone is used, the molecular weight of PHA produced tends to be large, as the above carbon source, (b) if glucose and the derivative thereof, and one or more of xylose, cellobiose, glucuronic acid, arabinose, mannose, galactose, sucrose, and derivatives thereof are used, the molecular weight of the PHA produced tends to be smaller than that in the case of (a) above, and as the above carbon source, (c) if one or more of xylose, cellobiose, glucuronic acid, arabinose, mannose, galactose, sucrose, and derivatives thereof, and none of glucose and/or the derivative thereof are used, the molecular weight of PHA produced tends to be even smaller than that in the case of (b) above.

A method for controlling a molecular weight of PHA by selecting such sugars as carbon source is also provided by the present invention. The method for controlling a molecular weight of PHA according to the present invention is a method wherein a carbon source for the culturing comprises a sugar or sugars selected from:

(a) glucose and/or a derivative thereof alone, (b) glucose and the derivative thereof as well as one or more of xylose, cellobiose, glucuronic acid, arabinose, mannose, galactose, sucrose, and derivatives thereof, or (c) one or more of xylose, cellobiose, glucuronic acid, arabinose, mannose, galactose, sucrose, and the derivatives thereof, to control a weight-average molecular weight of the polyhydroxy alkanoic acid produced between 1 million and 6 million.

As the control method of the present invention, a method for controlling a molecular weight of PHA to a weight-average molecular weight of 1 million to 5.75 million is preferable.

The amount of a sugar (initial concentration of culture) used in the production method of the present invention is not limited, an example being about 5 g/L to 910 g/L. The amount of sugar preferably is about 5 g/L to about 500 g/L and more preferably is about 10 g/L to 50 g/L.

In the production method of the present invention, the sugar used may be fed separately in a plural times. The number of times and timing of feeding are not limited, and the number of times may be 2, 3, 4, 5, or 6 or more.

The timing of feeding after the start of culturing may be selected from among after about 20 hours to about 30 hours, after about 30 hours to about 40 hours, after about 40 hours to about 50 hours, after about 50 hours to about 60 hours, after about 60 hours to about 70 hours, after about 70 hours to about 80 hours, or after about 80 hours, and the sugar can be fed by combining each selected timing.

In the production method of the present invention, as described above, by adding a furfural compound as a further carbon source, a PHA can be produced by controlling a molecular weight of PHA to a wider range of molecular weights, a weight-average molecular weight of 200,000 to 6 million, for example. More specifically, the present invention also relates to the following each invention:

A method for producing a polyhydroxy alkanoic acid comprising culturing a microorganism to obtain the polyhydroxy alkanoic acid as a culture product, wherein a carbon source for the culturing comprises a furfural compound together with a sugar or sugars selected from:
(a) glucose and/or a derivative thereof alone,
(b) glucose and a derivative thereof as well as one or more of xylose, cellobiose, glucuronic acid, arabinose, mannose, galactose, sucrose, and derivatives thereof, or
(c) one or more of xylose, cellobiose, glucuronic acid, arabinose, mannose, galactose, sucrose, and the derivatives thereof,
to obtain polyhydroxy alkanoic acid.

A method for culturing a microorganism and controlling a molecular weight of a polyhydroxy alkanoic acid obtained as a culture product,
wherein a carbon source for the culturing comprises a furfural compound together with a sugar or sugars selected from:
(a) glucose and/or a derivative thereof alone,
(b) glucose and a derivative thereof as well as one or more of xylose, cellobiose, glucuronic acid, arabinose, mannose, galactose, sucrose, and derivatives thereof, or
(c) one or more of xylose, cellobiose, glucuronic acid, arabinose, mannose, galactose, sucrose, and the derivatives thereof,
to control a weight-average molecular weight of the polyhydroxy alkanoic acid produced.

A furfural compound is a type of aldehyde produced from a saccharide as a raw material, and it is known that 5-hydroxymethylfurfural (HMF) is produced from hexose and furfural is produced from pentose, by heating the saccharide under an acidic condition or the like. Among furfural compounds, "furfural" is a common name for 2-furyl aldehyde.

The "furfural compound" in the present invention refers to furfural and 5-hydroxymethylfurfural as well as derivatives thereof.

In the present invention, further by using a furfural compound in addition to the aforementioned saccharide, in particular glucose and/or a derivative thereof, above all glucose alone as a carbon source, a molecular weight of the obtained PHA can further be reduced and controlled. For example, further by using the furfural compound, the molecular weight of the obtained PHA can be controlled to 200,000 to 5.5 million, and can be controlled to 200,000 to 4 million, or 200,000 to 3.61 million.

Without being bound by any theory, the reason why a PHA can be produced under control of a molecular weight of PHA over a wider range of molecular weights by the furfural compound, may be due to the furfural compound facilitating a transfer reaction of polymer chains formed by a polymerization. It could be that when a polymer is formed by polymerization, since elongation of the polymer chain is terminated by promoting transfer of a propagating end of a polymer chain having a relatively low molecular weight by the furfural compound, and elongation of the next polymer chain different from the polymer is initiated, a molecular weight of the obtained PHA is smaller than that in the case where the furfural compound is not used.

The type of furfural compound used in the production method or control method of the present invention using the furfural compound, is not limited, and furfural, 5-hydroxymethylfurfural, and derivatives thereof are exemplified. As such derivatives, for example, 5-hydroxymethylfurancarboxylic acid, 5-hydroxyfurfuryl alcohol, furan-2,5-bismethanol and an etherified or an esterified compound thereof are recited. A methoxylated compound is exemplified as the etherified compound, and acetylated and methyl esterified compounds are each exemplified as the esterified compound.

A preferable production method or the control method of the present invention includes a method wherein the sugars are glucose and a derivative thereof as well as one or more of xylose, cellobiose, glucuronic acid, arabinose, mannose, galactose, sucrose, and derivatives thereof, and furfural compounds are furfural and/or 5-hydroxymethylfurfural or derivatives thereof.

An amount of the furfural compound used in the production method of the present invention is not limited, an example of an initial concentration thereof in a culture being about 0.01 to about 3.0 g/L. The initial concentration of the furfural compound is preferably 0.01 g/L to 1 g/L.

A ratio of the amount of furfural compound used to an amount of a sugar used is not limited, an example being about 0.0025 to about 0.6. A preferable production method or the control method of the present invention include a method wherein the ratio of the amount of the furfural compound used to the amount of the sugar is 0.01 to 0.2.

<Microorganism>

In the production method of the present invention, a PHA can be produced by culturing a microorganism by a known method.

The microorganism used in the production method of the present invention is not limited, a highly halophilic bacterium being suitable as the microorganism because not only the production capacity of PHA is high, but also the produced PHA is easy to recover.

Among the highly halophilic bacteria, those belonging to genus *Haloferax*, genus *Halalkalicoccus*, genus *Haloarchaeobius*, genus *Haloarcula*, genus *Halobacterium*, genus *Halobaculum*, genus *Halococcus*, genus *Halogranum*, genus *Halomarina*, genus *Halorubrum*, genus *Haloterrigena*, genus *Natrialba*, and genus *Natronobacterium* are preferable with *Haloferax mediterranei* being particularly preferable.

In the control method of the present invention, the microorganism used in the production method of the present invention can also be used.

<Other Culture Conditions>

For the culturing of a microorganism in the method for producing a PHA of the present invention, conditions other than the above carbon source and microorganism are not limited, and conditions normally used in this technical field and known conditions may be used.

A medium used for the culture in the production method of the present invention may be a solid, liquid, or a gel, a liquid medium being preferable from the viewpoint of production rate.

For the culturing in the production method of the present invention, a total salt concentration includes, for example, 100 g/L to 300 g/L; the total salt concentration is preferably 150 g/L to 250 g/L.

The medium used is, for example, a medium containing inorganic salts such as $NH_4Cl$, $KH_2PO_4$, $FeCl_3$, $NaCl$, $MgCl_2$, $MgSO_4$, $CaCl_2$, $KCl$, $NaHCO_3$ and $NaBr$. Types and amounts of these inorganic salts are not limited, and for example, for $NH_4Cl$, $KH_2PO_4$, $FeCl_3$, $KCl$, $NaHCO_3$, $NaBr$, and $NaCl$, the following amounts (g/L) thereof are recited as examples:

$NH_4Cl$: 1.5 to 2.5, $KH_2PO_4$: 0.005 to 0.35, $FeCl_3$: 0.001 to 0.01, $KCl$: 3 to 7, $NaHCO_3$: 0.1 to 1, $NaBr$: 0.3 to 0.7, $NaCl$: 100 to 300.

As the medium used in the method for producing a PHA of the present invention, a preferable one is the medium of No. 1380 in a list of media published on the website (nite.go.jp/nbrc/cultures/cultures/culture-list.html) of NBRC (National Institute of Technology and Evaluation, Biological Resource Center). The medium composition of said No. 1380 is shown by excerpting from the above-mentioned medium list:

Medium No. 1380
Medium Halo 2 g

Composition

| | |
|---|---|
| Glucose | 1.8 g |
| Bacto Yeast Extract (Difco) | 0.1 g |
| Casamino acids | 0.1 g |
| Sodium glutamate | 1 g |
| Trisodium citrate | 1 g |
| KCl | 2 g |
| $K_2HPO_4$ | 0.3 g |
| $CaCl_2 \cdot 2H_2O$ | 0.15 g |
| $NH_4Cl$ | 1 g |
| $MgSO_4 \cdot 7H_2O$ | 50 g |
| NaCl | 200 g |
| Trace elements solution* | 2 ml |
| Agar (if needed) | 20 g |
| Distilled water | 1 L |
| | pH 7.0-7.4 |

After autoclaving, add filter-sterile glucose solution.

*Trace elements solution

| | |
|---|---|
| Nitrilotriacetic acid (NTA) | 12.8 g |
| $FeCl_3 \cdot 6H_2O$ | 1.35 g |
| $MnCl_2 \cdot 4H_2O$ | 0.1 g |
| $CoCl_2 \cdot 6H_2O$ | 0.024 g |
| $CaCl_2 \cdot 2H_2O$ | 0.1 g |
| $ZnCl_2$ | 0.1 g |
| $CuCl_2 \cdot 2H_2O$ | 0.025 g |
| $H_3BO_3$ | 0.01 g |
| $Na_2MoO_4 \cdot 2H_2O$ | 0.024 g |
| NaCl | 1 g |
| $NiCl_2 \cdot 6H_2O$ | 0.12 g |
| Distilled water | 1 L |

First dissolve nitrilotriacetic acid and adjust pH to 6.5 with NaOH, and then add minerals.
Final pH 7.0.

Comment

A nutrient source contained in a medium used for culturing a microorganism in the production method of the present invention will be further explained below, and as described above, at least any one of the sugars defined in the above (a) to (c) is used as the carbon source; as a carbon source different from the aforementioned sugars for culturing a microorganism, carbon sources ordinarily used for culturing a microorganism such as amino acids, alcohols, fats and oils, and/or fatty acids and the like, may be used. The following are specifically exemplified:

As the amino acids, glycine, alanine, phenylalanine, lysine, and leucine;
as the alcohols, methanol, ethanol, 1-propanol, 2-propanol, and glycerol;
as the fats and oils, palm oil, palm kernel oil, corn oil, coconut oil, olive oil, soybean oil, and rapeseed oil; and
as the fatty acids, acetic acid, propionic acid, butyric acid, valeric acid, caproic acid, and crotonic acid as well as fatty acid salts such as a sodium salt and an ammonium salt thereof, are exemplified. When fatty acids are used, small amounts of the fatty acids are preferable.

The medium used for culturing a microorganism in the production method of the present invention may comprise nitrogen sources, inorganic salts, and the like.

As the nitrogen source, for example, ammonium salts such as ammonia, ammonium chloride, ammonium sulfate, and ammonium phosphate, as well as peptone, a meat extract, a yeast extract, and the like are recited.

As the inorganic salts, for example, potassium dihydrogen phosphate, disodium hydrogen phosphate, magnesium phosphate, magnesium sulfate, sodium chloride, and the like are recited.

A culture temperature in culturing microorganisms in the production method of the present invention is not limited as long as the temperature allows the microorganism to grow, an example being about 10° C. to about 65° C.; 20° C. to 50° C. is preferable, and 35° C. to 45° C. is more preferable.

In the production method of the present invention, timings of adding carbon sources, inorganic salts, and organic nutrient sources are not limited; commonly used methods such as batch culture, fed-batch culture, and continuous culture can be selected and used in accordance with the purposes.

As a culture time for culturing a microorganism in the production method of the present invention such as 24 hours to 168 hours for the batch culture, 72 hours to 14 days for the fed-batch culture, or a long period of longer than 14 days for the continuous culture, is recited without being limited thereto.

In the production method of the present invention, increasing an amount of dissolved oxygen in a medium is preferable, maintaining the amount of dissolved oxygen in the medium at a saturated amount being more preferable.

A pH of a medium is not limited in the production method of the present invention; an initial pH of the medium preferable is about 6.5 to about 7.5. More preferable is the initial pH of the medium being about 6.5 to about 7.5 and a pH of the medium while culturing being maintained at about 6.5 to about 7.5. The pH thereof is further preferably set to about 7.0 to about 7.4.

In the control method of the present invention, other culture conditions used in the production method of the present invention can also be employed.

<PHA Produced by the Production Method of the Present Invention>

The type of PHA, which is a product in the production method of the present invention, is not limited; a PHBV and/or a P(3HB) (3-hydroxybutanoic acid polymer) are preferable products.

The PHA produced by the production method of the present invention can be recovered from bacterial cells by known methods with centrifugation and filtration/precipitation using an organic solvent, a surfactant, a low-concentration sodium chloride aqueous solution or water.

An amount and a 3HV fraction of PHA produced by a microorganism in the production method of the present invention may be measured by using a known method such as a GC-MS method. When the PHA obtained by the production method of the present invention is a PHBV, the 3HV fraction may also be determined by using a known method such as the GC-MS method.

For measuring concentrations of glucose or a derivative thereof, other saccharides, and furfural compounds, a measurement using a commercially available concentration measurement kit or a known method such as an HPLC method may be used.

When it is necessary to specify an amount of microbial cells produced in culturing the microorganism in the production method of the present invention, the amount of the microbial cells produced may be measured by known methods such as an absorbance method and a dry microbial cell weight measurement method.

A molecular weight of PHA obtained by the production method of the present invention may also be measured by a known method; for example, by gel permeation chromatography using a polystyrene standard. As described above, for the molecular weight of PHA in the present description, numerical values measured by gel permeation chromatography using a polystyrene standard are used unless otherwise stated.

The weight-average molecular weight of PHA produced by the method of the present invention is about 1 million to about 6 million when the furfural compound is not used, and it is about 200,000 to about 6 million when the furfural compound is used. The molecular weight of PHA obtained in each range can be controlled or adjusted in the production method of the present invention.

2. PHBV

By the present invention, a copolymer wherein 3-hydroxybutanoic acid (3HB) and 3-hydroxyvaleric acid (3HV) are randomly copolymerized (hereinafter may be referred to as "PHBV") is also provided, said PHBV having a weight-average molecular weight of more than 3.61 million, and preferably more than 4 million. A PHBV of the present invention having a molecular weight of more than 5 million is more preferable, and a PHBV having a molecular weight of more than 5.7 million is further preferable.

The PHBV of the present invention comprises the structural units shown below as any combination thereof wherein a molecular weight of the entire PHBV exceeds 3.61 million wherein m and n denote integers in the formula below:

[Formula 1]

The structure, the composition of the monomer, and the molecular weight of PHBV of the present invention are not limited as long as the molecular weight exceeds 3.61 million. The PHBV of the present invention is linear, and the PHBV of the present invention at least substantially linear is preferable.

The PHBV of the present invention is a copolymer wherein the 3HB and the 3HV are randomly copolymerized as described above; a copolymer formed by alternating copolymerization or block copolymerization of the 3HB and the 3HV is also included.

For the PHBV of the present invention, a molar ratio of 3-hydroxybutanoic acid and 3-hydroxyvaleric acid constituting the PHBV is not limited. The PHBV of the present invention preferably has a 3HV fraction (a molar percentage of 3-hydroxyvaleric acid based to the total moles of 3-hydroxybutanoic acid and 3-hydroxyvaleric acid constituting the copolymer) of about 5.0% to about 40.0%, the PHBV of the present invention more preferably has the 3HV fraction of about 5.0% to about 28.0%, the PHBV of the present invention further preferably has the 3HV fraction of about 7.0% to about 18.0%, and the PHBV of the present invention even still further preferably has the 3HV fraction of about 9.0% to about 15.0%.

Of the PHBVs of the present invention, a PHBV having properties superior to conventional PHBVs, in particular, a PHBV that is more flexible than the conventional PHBVs and/or is superior in strength, is preferable. Among the PHBVs of the present invention, a PHBV having an excellent tensile strength is preferable.

Of the PHBVs of the present invention, a PHBV having a tensile strength that is further improved by cold-drawing is also preferable. A PHBV having a tensile strength of 240 MPa or more after cold-drawing is preferable, a PHBV having the tensile strength of 250 MPa or more is more preferable, and a PHBV having the tensile strength of 255 MPa or more is further preferable.

By the present invention, a cold-drawn film of a copolymer wherein 3-hydroxybutanoic acid and 3-hydroxyvaleric acid are randomly copolymerized and having a weight-average molecular weight of more than 3.61 million is also provided. Said film is has a feature of superior tensile strength as compared with a normal molecular weight PHBV having a weight-average molecular weight of 1 million.

Of the films of the present invention, a film having a tensile strength of 240 MPa or more is preferable, a film having the tensile strength of 250 MPa or more is more preferable, and a film having the tensile strength of 255 MPa or more is further preferable.

Moreover, the aforementioned film wherein cold drawing comprises the following steps is preferable because a film having an excellent tensile strength can more surely be obtained:

(1) obtaining a molten film by melting a copolymer formed by random copolymerization of 3-hydroxybutanoic acid and 3-hydroxyvaleric acid;

(2) rapidly cooling the molten film obtained in (1) in ice water to make an amorphous film;

(3) drawing the amorphous film obtained in (2) as it is in ice water to a 10-fold length to orient the amorphous film; and (4) subjecting the oriented film obtained in (3) to tension heat treatment to obtain a crystallized cold-drawn film.

Considering improvement of tensile strength by cold-drawing, a film having the 3HV fraction of 5% or more is preferable because the improvement of tensile strength by cold-drawing is remarkable. The reason is presumed that crystals comprising a 3HV component at a fraction of 5% or more exhibit the same strength as a PHB and can be melted at 170° C. The mechanism by which the effects of the present invention are exerted is not bound by such a theory. The PHBV of the present invention having the 3HV fraction of 5% to 15% is more preferable.

The method for producing the PHBV of the present invention is not limited, and any method capable of producing a PHBV having a weight-average molecular weight of more than 3.61 million may be employed.

As such a method, a method for culturing a microorganism to obtain the PHBV of the present invention as a culture product is recited; a method using highly halophilic bacteria as microorganism in the aforementioned culturing and using glucose and/or a derivative thereof as a carbon source is preferable and the method using glucose is particularly preferable. The reason is that, by these methods, a PHBV having a weight-average molecular weight of more than 3.61 million can efficiently be produced, and the PHBV produced can easily be recovered.

The method for producing the PHBV of the present invention is not limited; the PHBV can, for example, be produced by the aforementioned method for producing the PHA of the present invention. In the case of producing the PHBV of the present invention by using the aforementioned method for producing the PHA of the present invention, the sugars as a carbon source such as (a) glucose and/or a derivative thereof alone, or
(b) glucose and the derivative thereof as well as one or more of xylose, cellobiose, glucuronic acid, arabinose, mannose, galactose, sucrose, and derivatives thereof, may be used.

The PHBV of the present invention is produced by using a yeast extract even without adding a carbon source other than carbon sources such as amino acids contained in the yeast extract. By using the carbon source other than the carbon sources such as amino acids contained in the yeast extract, the PHBV of the present invention can be produced at a lower cost.

EXAMPLES

The present invention will be described in more detail by Examples. The present invention is not limited to said Examples in whatever manner.

In all the examples, experiments were carried out using a strain *Haloferax mediterranei* NBRC 14739 provided by NBRC unless otherwise stated.

Unless otherwise stated, in all the examples, after culturing the above bacteria under the methods and conditions shown in each Example, a molecular weight of PHA (PHBV) obtained by culturing was measured by GPC (gel permeation chromatography) using a polystyrene standard and shown as a molecular weight.

An EcoSEC HLC-8320GPC manufactured by Tosoh Corporation was used for GPC measurement. The guard column used was a TSKgel guardcolumn Super HZ-H, and the columns used were two TSK gel Super HZM-H columns connected in series. Chloroform (0.6 mL/min) was used as a mobile phase, and a column temperature was 40° C. A sample concentration was about 0.5 mg/mL, and a sample injection volume was 10 μL. Polystyrene standards were used to prepare a calibration curve.

A 3-hydroxyvaleric acid (3HV) fraction of a copolymer and an amount of PHBV produced were measured by using gas chromatography-mass spectrometry (GC-MS method) (apparatus name: Agilent 6890/5973 GCMS System) as follows. Namely, 2 ml of a sulfuric acid-methanol mixed solution (15:85) and 2 ml of chloroform were added to about 2 mg to 25 mg of dry bacterial cells, and the mixture was sealed and heated at 100° C. for 140 minutes to obtain methyl ester of a polyester decomposition product. After adding 1 mL of water thereto while stirring, a chloroform layer was analyzed by the GC-MS method.

These methods for measuring an amount produced, a molecular weight, and a 3HV fraction of these PHAs are those normally used in this technical field as methods for specifying the amount produced, the molecular weight, and the 3HV fraction of PHA. The values of the amount produced, the molecular weight, and the 3HV fraction of PHA specified by these methods are those which can accurately be compared with the values of the amount produced, the molecular weight, and the 3HV fraction of PHA described in the prior art documents, respectively.

A dry bacterial weight can be measured by a known method such as a freeze-drying method. When quantifying inorganic salts contained in the dry bacterial cells, a method for thermally decomposing all organic substances other than the inorganic salts at an elevated temperature may be used.

A. Examples 1 to 11 Flask Culture of *Haloferax mediterranei* NBRC14739

(Materials and methods) In a 300 mL Erlenmeyer flask, the following components were added so that a total volume of a culture solution was 50 mL, and shaking culture was carried out for 72 h at 37° C. and 200 rpm. The initial pH was adjusted to 7.2.

Ingredients in the medium (g/L):
$NH_4Cl$ 2, $KH_2PO_4$ 0.0375, $FeCl_3$ 0.005, NaCl 194, $MgCl_2$ 16, $MgSO_4$ 24, $CaCl_2$ 1, KCl 5, $NaHCO_3$ 0.2, NaBr 0.5, yeast extract 5.

To a medium (BSM medium) composed of the above components, predetermined amounts of sugars shown in the table below were added as carbon sources and the culturing was carried out for 72 h.

(Results) The table below clearly shows the 3HV fraction and the weight-average molecular weight, the polydispersity, the dry bacterial weight, and the amount of PHBV produced under each condition.

TABLE 1

|  | Initial glucose concentration (g/L) | Initial xylose concentration (g/L) | Initial cellobiose concentration (g/L) | 3HV fraction (%) | Mw (×10⁶) | Mw/Mn | Dry bacterial weight (g/L) | PHBV (g/L) |
| --- | --- | --- | --- | --- | --- | --- | --- | --- |
| Example 1 | 5 | 0 | 0 | 12.1 | 4.39 | 1.52 | 6.75 | 1.77 |
| Example 2 | 4 | 1 | 0 | 12.2 | 3.92 | 1.85 | 3.83 | 1.72 |
| Example 3 | 3 | 2 | 0 | 12.0 | 3.72 | 1.79 | 3.01 | 1.32 |
| Example 4 | 2 | 3 | 0 | 12.1 | 3.68 | 1.91 | 3.02 | 1.08 |
| Example 5 | 1 | 4 | 0 | 13.0 | 2.48 | 3.83 | 2.80 | 0.79 |
| Example 6 | 0 | 5 | 0 | 25.2 | 1.24 | 1.69 | 2.18 | 0.27 |
| Example 7 | 4 | 0 | 1 | 12.0 | 4.03 | 1.65 | 3.75 | 1.72 |
| Example 8 | 3 | 0 | 2 | 12.3 | 3.35 | 1.79 | 4.03 | 1.29 |
| Example 9 | 2 | 0 | 3 | 12.8 | 3.34 | 1.90 | 3.86 | 1.04 |
| Example 10 | 1 | 0 | 4 | 13.7 | 3.42 | 1.72 | 3.13 | 0.69 |
| Example 11 | 0 | 0 | 5 | 20.2 | 3.52 | 1.71 | 2.37 | 0.40 |

As clearly shown in the above table, by changing the types of saccharides, the molecular weight of PHBV can be controlled from 4.39 million to 1.24 million and the 3HV fraction can be controlled from 12.0% to 25.2%.

B. Example 12-1 (Scale-Up Test-1)

(Materials and methods) Using a 5 L volume jar fermenter, the following components were added for culturing in 2 L for 146 h at 37° C. and an initial glucose concentration of 20 g/L. During the culturing, the pH was maintained at 7.2 by using 12% aqueous ammonia, and the culturing was carried out until glucose was totally consumed.

Ingredients in the medium (g/L):
$NH_4Cl$ 2, $KH_2PO_4$ 0.0375, $FeCl_3$ 0.005, NaCl 194, $MgCl_2$ 16, $MgSO_4$ 24, $CaCl_2$ 1, KCl 5, $NaHCO_3$ 0.2, NaBr 0.5, yeast extract 5.

(Results/Discussion) The table below shows, for each culture time, the 3HV fraction and the weight-average molecular weight, the polydispersity, the dry bacterial weight, and the amount produced of PHBV.

TABLE 2

| Culture time (h) | 3HV fraction (%) | Mw (×10$^6$) | Mw/Mn | Dry bacterial weight (g/L) | PHBV (g/L) |
|---|---|---|---|---|---|
| 24 | 12.8 | 3.64 | 1.64 | 2.72 | 0.33 |
| 31 | 12.2 | 3.20 | 1.80 | 2.74 | 0.50 |
| 47.5 | 9.7 | 4.01 | 1.70 | 4.31 | 1.20 |
| 55 | 8.6 | 4.50 | 1.67 | 4.69 | 1.53 |
| 72 | 7.3 | 4.80 | 1.48 | 6.16 | 2.30 |
| 79 | 7.3 | 4.70 | 1.72 | 5.41 | 2.41 |
| 143 | 6.2 | 4.80 | 1.63 | 7.99 | 4.10 |
| 146 | 6.2 | 5.04 | 1.47 | 7.71 | 3.98 |

As shown in the above table, by expanding the scale of the culture vessel and controlling the pH during the culturing, the amount of PHBV produced was increased and the production efficiency was improved.

C. Example 12-2 (Scale-Up Test-2: Study on Adding Ingredient)

(Materials and methods) Using a 5 L volume jar fermenter, the following components were added for culturing in 2 L for 288 h at 37° C. and an initial glucose concentration of 20 g/L. During the culturing, the pH was maintained at 7.2 by using 12% aqueous ammonia, 40 g of glucose was further added at 96 h after the start of culturing, and 0.075 g of KH$_2$PO$_4$ was further added at 168 h.

Ingredients in the medium (g/L):
NH$_4$Cl 2, KH$_2$PO$_4$ 0.0375, FeCl$_3$ 0.005, NaCl 194, MgCl$_2$ 16, MgSO$_4$ 24, CaCl$_2$ 1, KCl 5, NaHCO$_3$ 0.2, NaBr 0.5, yeast extract 5.

(Results) The table below shows, for each culture time, the 3HV fraction and the weight-average molecular weight, the polydispersity, the dry bacterial weight, and the amount produced of PHBV.

TABLE 3

| Culture time (h) | 3HV fraction (%) | Mw (×10$^6$) | Mw/Mn | Dry bacterial weight (g/L) | PHBV (g/L) |
|---|---|---|---|---|---|
| 72 | 7.2 | 4.96 | 1.59 | 6.64 | 3.29 |
| 96 | 6.8 | 5.02 | 1.52 | 8.06 | 4.45 |
| 104 | 6.8 | 5.03 | 1.51 | 7.98 | 2.59 |
| 120 | 6.3 | 5.21 | 1.44 | 8.72 | 4.43 |
| 144 | 6.4 | 5.14 | 1.45 | 9.62 | 5.62 |
| 168 | 6.9 | 5.08 | 1.45 | 7.83 | 4.72 |
| 175 | 7.0 | 4.84 | 1.45 | 6.70 | 4.88 |
| 176 | 7.2 | 4.16 | 1.71 | 15.92 | 12.48 |
| 240 | 7.3 | 3.91 | 1.92 | 5.45 | 3.63 |
| 264 | 9.8 | 3.50 | 1.76 | 5.59 | 3.87 |
| 288 | 10.2 | 3.50 | 1.88 | 7.08 | 4.73 |

The molecular weight of PHBV increased as compared with that of Example 12-1; the amount of PHBV produced was further increased by adding glucose, and reached the maximum value at 175 hours to 176 hours after the start of culturing.

D. Example 12-3 (Scale-Up Test-3: Study on Amount of Sugar (1))

(Materials and methods) Using a 5 L volume jar fermenter, the following components were added for culturing in 2 L for 168 h at 37° C. and an initial glucose concentration of 40 g/L. During the culturing, the pH was maintained at 7.2 with 12% aqueous ammonia.

Ingredients in medium (g/L):
NH$_4$Cl 2, KH$_2$PO$_4$ 0.0375, FeCl$_3$ 0.005, NaCl 194, MgCl$_2$ 16, MgSO$_4$ 24, CaCl$_2$ 1, KCl 5, NaHCO$_3$ 0.2, NaBr 0.5, yeast extract 5.

(Results) The table below shows the 3HV fraction and the weight-average molecular weight, the polydispersity, the dry bacterial weight, and the amount produced of PHBV for each hour.

TABLE 4

| Culture time (h) | 3HV fraction (N | Mw (×10$^6$) | Mw/Mn | Dry bacterial weight (g/L) | PHBV (g/L) |
|---|---|---|---|---|---|
| 24 | 15.1 | 1.58 | 2.24 | 6.04 | 0.86 |
| 48 | 9.0 | 3.03 | 2.34 | 9.17 | 2.71 |
| 72 | 7.9 | 3.86 | 2.00 | 13.53 | 3.96 |
| 144 | 8.3 | 4.33 | 2.01 | 11.22 | 4.88 |
| 168 | 8.4 | 4.38 | 1.87 | 12.18 | 4.91 |

As shown in the above table, the production efficiency of PHBV was improved as compared with that of Example 12-2. because the reason was presumed that the amount of sugar at the start of culturing was increased.

E. Example 12-4 (Scale-Up Test-4: Examination of Amount of Sugar (2))

(Materials and methods) Using a 5 L volume jar fermenter, the following components were added for culturing in 2 L for 288 h at 37° C. and an initial glucose concentration of 80 g/L. During the culturing, the pH was maintained at 7.2 with 12% aqueous ammonia.

Ingredients in medium (g/L):
NH$_4$Cl 2, KH$_2$PO$_4$ 0.0375, FeCl$_3$ 0.005, NaCl 194, MgCl$_2$ 16, MgSO$_4$ 24, CaCl$_2$ 1, KCl 5, NaHCO$_3$ 0.2, NaBr 0.5, yeast extract 5.

(Results/Discussion) The table below shows the 3HV fraction and the weight-average molecular weight, the polydispersity, the dry bacterial weight, and the amount produced of PHBV for each hour.

TABLE 5

| Culture time (h) | 3HV fraction (N | Mw (×10$^6$) | Mw/Mn | Dry bacterial weight (g/L) | PHBV (g/L) |
|---|---|---|---|---|---|
| 24 | 16.4 | 3.98 | 1.92 | 5.87 | 1.21 |
| 72 | 9.0 | 4.60 | 1.91 | 7.91 | 4.38 |
| 168 | 7.2 | 4.42 | 1.91 | 12.24 | 5.17 |
| 216 | 7.6 | 4.12 | 1.80 | 11.70 | 4.11 |
| 240 | 9.0 | 3.88 | 2.07 | 9.74 | 2.23 |

As shown in the above table, there was no improvement in the production efficiency of PHBV as compared with that of Example 12-3.

F. Example 12-5 (Scale-Up Test-5: Study on Medium)

Example A (Materials and methods) Using a 5 L jar fermenter, the following components were added for culturing in 2 L for 144 h at 37° C. and an initial glucose concentration of 10 g/L. During the culturing, the pH was maintained at 7.2 by using 12% aqueous ammonia, and nutrient sources and inorganic salts were appropriately added during the culturing.

Ingredients (g/L) in the medium at the start of culturing:
Glucose 10, yeast extract 0.1,
casamino acid 0.1,
monosodium glutamate monohydrate 1,
sodium citrate dihydrate 1,
KCl 2, $K_2HPO_4$ 0.3,
$CaCl_2 \cdot 2H_2O$ 0.15, $NH_4Cl$ 1,
$MgSO_4 \cdot 7H_2O$ 50, NaCl 200,
other trace metal elements.

As the other trace metal elements, those contained in the designated medium No. 1380 published by NBRC were used. More specifically, 12.8 g of nitrilotriacetic acid, 1.35 g of iron (III) chloride hexahydrate, 0.1 g of manganese chloride tetrahydrate, 0.024 g of cobalt chloride hexahydrate, 0.1 g of calcium chloride dihydrate, 0.1 g of zinc chloride, 0.025 g of copper (II) chloride dihydrate, 0.01 g of boric acid, 0.024 g of sodium molybdate dihydrate, 1 g of sodium chloride, 0.12 g of nickel chloride hexahydrate, and 1 L of water, were dissolved so that a pH thereof was 7.0, and added at a concentration of 2 mL/L (culture solution).

The added ingredient (g/L) was:
after 30 h from the start of culturing; glucose 10,
after 48 h; glucose 10,
after 56 h; glucose 10,
after 74 h; glucose 10 and yeast extract 0.1,
casamino acid 0.1,
monosodium glutamate monohydrate 1,
sodium citrate dihydrate 1, KCl 2, and
$CaCl_2 \cdot 2H_2O$ 0.15,
after 80 h; glucose 10.

(Result) The result is as shown in the table below.

These results clearly show that the maximum weight-average molecular weight of 5.72 million is obtained, and 11.58 g/L of PHBV is produced.

TABLE 6

| Culture time (h) | 3HV fraction (%) | DCW (g/L) | PHBV concentration (g/L) | Mw × 10^6 | Mw/Mn |
|---|---|---|---|---|---|
| 24 | 13.70 | 2.48 | 0.52 | 4.79 | 1.63 |
| 48 | 8.28 | 8.22 | 4.81 | 5.49 | 1.68 |
| 72 | 8.72 | 13.44 | 7.85 | 5.72 | 1.52 |
| 144 | 10.26 | 18.38 | 10.70 | 5.24 | 1.88 |
| 168 | 10.68 | 18.90 | 11.58 | 5.21 | 1.58 |

G. Example 12-6 (Scale-Up Test-6: Study on Sugar Feeding)

Example B (Materials and methods) Using a 5 L jar fermenter, the following components were added for culturing in 2 L for 144 h at 37° C. and an initial glucose concentration of 10 g/L. During the culturing, the pH was maintained at 7.2 by using 12% aqueous ammonia, and nutrient sources and inorganic salts were appropriately added during the culturing.

Ingredients (g/L) in the medium at the start of culturing:
Glucose 10, yeast extract 0.1,
casamino acid 0.1,
monosodium glutamate monohydrate 1,
sodium citrate dihydrate 1,
KCl 2, $K_2HPO_4$ 0.3,
$CaCl_2 \cdot 2H_2O$ 0.15, $NH_4Cl$ 1,
$MgSO_4 \cdot 7H_2O$ 50, NaCl 200,
other trace metal elements.

As the other trace metal elements, those as described above contained in the designated medium No. 1380 published by NBRC were used.

Amounts added (g/L) were,
30 h after from the start of culturing; glucose 20,
54 h after; glucose 20, yeast extract 0.1,
casamino acid 0.1,
monosodium glutamate monohydrate 1,
sodium citrate dihydrate 1,
KCl 2, and $CaCl_2 \cdot 2H_2O$ 0.15,
79 h after; glucose 30.

(Result) The results are as shown in the table below.

These results clearly show that production of PHBV having the maximum weight-average molecular weight of 5.41 million at 12.3 g/L of is at least possible.

TABLE 7

| Culture time (h) | 3HV fraction (%) | DCW (g/L) | PHBV concentration (g/L) | Mw × 10^6 | Mw/Mn |
|---|---|---|---|---|---|
| 24 | 13.7 | 1.55 | 0.22 | | |
| 48 | 7.7 | 8.10 | 4.43 | 5.25 | 1.74 |
| 72 | 8.3 | 12.60 | 7.90 | 5.41 | 1.63 |
| 144 | 9.7 | 18.61 | 12.28 | 5.22 | 1.69 |

H. Example 12-7 (Scale-Up Test-7: Examination of Production Conditions)

(Materials and methods) Using a 5 L jar fermenter, the following components were added for culturing in 2 L for 72 h at 37° C. and an initial glucose concentration of 6.8 g/L. The initial pH was maintained at 7.2, and during the culturing, the pH was not controlled, and no nutrient sources or inorganic salts were added.

Ingredients (g/L) in the medium at the start of culturing:
Glucose 6.8, yeast extract 0.1,
casamino acid 0.1,
monosodium glutamate monohydrate 1,
sodium citrate dihydrate 1,
KCl 2, $CaCl_2 \cdot 2H_2O$ 0.15, $NH_4Cl$ 1,
$MgSO_4 \cdot 7H_2O$ 50, NaCl 200,
other trace metal elements.

As the other trace metal elements, those as described above, described in the designated medium No. 1380 published by NBRC were used.

(Result) The results are as shown in the table below.

These results clearly show that, by not controlling the pH, the PHBV with the high 3HV fraction is produced.

TABLE 8

| Culture time (h) | 3HV fraction (%) | DCW(g/L) | PHBV concentration (g/L) | Mw × 10^6 | Mw/Mn |
|---|---|---|---|---|---|
| 24 | 21.2 | 1.13 | 0.245 | 5.09 | 1.66 |
| 48 | 30.0 | 2.73 | 1.08 | 534 | 1.74 |
| 72 | 30.3 | 3.56 | 2.01 | 551 | 1.59 |

I. Examples 13 and 14 Flask Culture of *Haloferax mediterranei* NBRC14739 (Study on Yeast Extract)

(Materials and methods) In a 300 mL Erlenmeyer flask, the following components were added so that a total volume of a culture solution was 50 mL, and shaking culture was carried out for 72 h at 37° C. and 200 rpm. The initial pH was adjusted to 7.2.

Ingredients in the medium (g/L):
$NH_4Cl$ 2, $KH_2PO_4$ 0.0375, $FeCl_3$ 0.005, NaCl 194, $MgCl_2$ 16, $MgSO_4$ 24, $CaCl_2$ 1, KCl 5, $NaHCO_3$ 0.2, NaBr 0.5.

To each medium composed of the above components, a yeast extract and the sugars were added in predetermined amounts and the culturing was carried out for 72 h.

(Results/Discussion) The table shows the 3HV fraction and the weight-average molecular weight, the polydispersity, the dry bacterial weight, and the amount of PHBV produced under each condition.

TABLE 9

| | Sugar [concentration] (g/L) | Yeast extract concentration (g/L) | 3HV fraction (%) | Mw (×10⁶) | Mw/Mn | Dry bacterial weight (g/L) | PHBV (g/L) |
|---|---|---|---|---|---|---|---|
| Example 13 | glucose [5] | 1 | 23.6 | 4.33 | 1.70 | 1.33 | 0.20 |
| Example 14 | none | 5 | 33.9 | 5.04 | 1.40 | 1.68 | 0.21 |

The PHBV of the present invention was also produced when the yeast extract alone was used, and no sugar was added.

J. Example 15 <Evaluation of Medium>

(Materials and methods) For *Haloferax mediterranei*, culturing was carried out using the NBRC-designated medium for the highly halophilic bacteria shown in Table 10+5 g/L of glucose with a total culture solution volume of 50 mL in a 300 mL Erlenmeyer flask. When glucose was contained in the designated medium, 5 g/L of glucose was further added in addition to the glucose originally contained.

The ingredients of each designated medium are shown below by excerpting the medium list (nite.go.jp/nbrc/cultures/culture-list.html) published on the website of NBRC.

| Medium No. | 255 |
|---|---|
| Medium Composition | |
| Bacto Casamino Acids (Difco) | 7.5 g |
| Yeast Extract | 10 g |
| Trisodium citrate | 3 g |
| KCl | 2 g |
| $MgSO_4 \cdot 7H_2O$ | 20 g |
| $FeSO_4 \cdot 7H_2O$ | 0.05 g |
| $MnSO_4 \cdot nH_2O$ | 0.2 mg |
| NaCl | 250 g |
| Distilled water | 1 L |
| Agar (if needed)* | 20 g |
| | pH 7.4 |
| Comment | |

*Dissolve agar by heating before adding NaCl.

| Medium No. | 257 |
|---|---|
| Medium Composition | |
| NaCl | 156 g |
| $MgCl_2 \cdot 6H_2O$ | 13 g |
| $MgSO_4 \cdot 7H_2O$ | 20 g |
| $CaCl_2 \cdot 2H_2O$ | 1 g |
| KCl | 4 g |
| $NaHCO_3$ | 0.2 g |
| KBr | 0.5 g |
| Yeast Extract | 5 g |
| Glucose | 1 g |
| Distilled water | 1 L |
| Agar (if needed)* | 20 g |
| | pH 7.0 |
| Comment | |

| Medium No. | 865 |
|---|---|
| Medium | *Harcarcula* Medium |
| Composition | |
| Casamino Acids (Difco) | 5 g |
| Bacto Yeast Extract (Difco) | 5 g |
| Sodium glutamate | 1 g |
| Trisodium citrate | 3 g |
| $MgSO_4 \cdot 7H_2O$ | 20 g |
| KCl | 2 g |
| NaCl | 200 g |
| $FeCl_2 \cdot 4H_2O$ | 36 mg |
| $MnCl_2 \cdot 4H_2O$ | 0.26 mg |
| Distilled water | 1 L |
| Agar (if needed) | 20 g |
| | pH 7.0-7.2 |
| Comment | |

| Medium No. | 258 |
|---|---|
| Medium Composition | |
| NaCl | 125 g |
| $MgCl_2 \cdot 6H_2O$ | 160 g |
| $CaCl_2 \cdot 2H_2O$ | 0.13 g |
| $K_2SO_4$ | 5 g |
| Hipolypepton* | 1 g |
| Yeast Extract | 1 g |
| Soluble starch | 2 g |
| Distilled water | 1 L |
| Agar (if needed) | 15 g |
| | pH 7.0 |
| Comment | |

*Wako Pure Chemical Ind., Ltd., Osaka, Japan.

| Medium No. | 368 |
|---|---|
| Medium | |
| Composition | |
| Yeast Extract | 10 g |
| Casamino Acids | 7.5 g |
| NaCl | 250 g |
| $MgSO_4 \cdot 7H_2O$ | 40 g |
| KCl | 2 g |
| Trisodium citrate | 3 g |
| $FeCl_3 \cdot 4H_2O$ | 36 mg |
| $MnCl_2 \cdot 4H_2O$ | 0.36 mg |
| Distilled water, make up to | 1 L |
| Agar* (if needed) | 20 g |
| | pH 7.2 |
| Comment | |

*Dissolve agar by heating before adding NaCl.

| Medium No. | 1214 |
|---|---|
| Medium | *Halomarina* medium |
| Composition | |
| Casamino Acids | 1 g |
| Bacto Yeast Extract (Difco) | 1 g |
| NaCl | 150 g |
| Agar | 15 g |
| Artificial seawater | 1 L |
| | pH 7.5 |
| Comment | |

| Medium No. | 1338 |
|---|---|
| Medium | NSSM medium |
| Composition | |
| Bacto Yeast Extract (Difco) | 1 g |
| Casamino Acids | 1 g |
| Bacto Proteose Peptone No. 3 (Difco) | 3 g |
| Glucose | 1 g |
| Sodium pyruvate | 0.05 g |
| NaCl | 132 g |
| K2HPO4 | 0.6 g |
| Agar (if needed) | 20 g |
| Artificial seawater | 1 L |
| | pH 7.0-7.2 |
| Comment | |

| Medium No. 1380 | |
|---|---|
| Medium Halo 2 g | |
| Composition | |
| Glucose | 1.8 g |
| Bacto Yeast Extract (Difco) | 0.1 g |
| Casamino acids | 0.1 g |
| Sodium glutamate | 1 g |
| Trisodium citrate | 1 g |
| KCl | 2 g |
| $K_2HPO_4$ | 0.3 g |
| $CaCl_2 \cdot 2H_2O$ | 0.15 g |
| $NH_4Cl$ | 1 g |
| $MgSO_4 \cdot 7H_2O$ | 50 g |
| NaCl | 200 g |
| Trace elements solution* | 2 ml |
| Agar (if needed) | 20 g |
| Distilled water | 1 L |
| | pH 7.0-7.4 |
| After autoclaving, add filter-sterile glucose solution. | |

-continued

| Medium No. 1380 | |
|---|---|
| Medium Halo 2 g | |
| *Trace elements solution | |
| Nitrilotriacetic acid (NTA) | 12.8 g |
| $FeCl_3 \cdot 6H_2O$ | 1.35 g |
| $MnCl_2 \cdot 4H_2O$ | 0.1 g |
| $CoCl_2 \cdot 6H_2O$ | 0.024 g |
| $CaCl_2 \cdot 2H_2O$ | 0.1 g |
| $ZnCl_2$ | 0.1 g |
| $CuCl_2 \cdot 2H_2O$ | 0.025 g |
| $H_3BO_3$ | 0.01 g |
| $Na_2MoO_4 \cdot 2H_2O$ | 0.024 g |
| NaCl | 1 g |
| $NiCl_2 \cdot 6H_2O$ | 0.12 g |
| Distilled water | 1 L |
| First dissolve nitrilotriacetic acid and adjust pH to 6.5 with NaOH, and then add minerals. Final pH 7.0. | |

Comment (Result) The results are as shown in the table below.

By changing the media, production of PHA with the weight-average molecular weight range of 1.3 million to 5.4 million was possible.

The results clearly show that the medium of NBRC No. 1380 enables production of an unprecedented type of PHA having not only a high amount of PHA produced, but also a high 3HV fraction and a high molecular weight.

TABLE 10

| Medium | pH | DCW (g/L) | PHA (wt %) | 3HV (mol %) | Mn ($\times 10^6$) | Mw ($\times 10^6$) | Mw/Mn |
|---|---|---|---|---|---|---|---|
| BSM | 7.2 | 3.9 | 43.0 ± 7.4 | 12.1 | 2.7 | 4.4 | 1.6 |
| 255 | 7.2 | 5.7 | 27.5 | 16.6 | 0.94 | 1.6 | 1.7 |
| 257 | 7.0 | 4.5 | 48.0 | 9.5 | 2.8 | 4.5 | 1.6 |
| 865 | 7-7.2 | 2.8 | 33.7 | 27.4 | 1.5 | 2.6 | 1.8 |
| 258 | 7.0 | 3.7 | 34.8 | 14.5 | 2.4 | 4.1 | 1.7 |
| 368 | 7.2 | 4.3 | 3.8 | 27.2 | 0.81 | 1.3 | 1.6 |
| 1214 | 7.5 | 2.1 | 30.0 | 13.3 | 3.0 | 5.2 | 1.7 |
| 1338 | 7-7.2 | 1.2 | 24.1 | 17.1 | 2.3 | 4.5 | 1.9 |
| 1380 | 7-7.2 | 3.4 | 49.0 | 35.5 | 3.3 | 5.4 | 1.6 |

K. Examples 16 to 25 <Evaluation of Furfural Compound>

Flask culture of *Haloferax mediterranei* NBRC14739 was carried out at an initial glucose concentration of 10 g/L in the same manner as in Examples 1 to 11 except that a furfural compound was further used where a furfural concentration or an HMF (5-hydroxymethylfurfural) concentration was changed from 0.06 g/L to 1.6 g/L. More specific procedures were as follows.

(Materials and methods) In a 300 mL Erlenmeyer flask, the following components were added so that a total volume of a culture solution was 50 mL, and shaking culture was carried out for 72 h at 37° C. and 200 rpm. The initial pH was adjusted to 7.2.

Ingredients in the medium (g/L):
$NH_4Cl$ 2, $KH_2PO_4$ 0.0375, $FeCl_3$ 0.005, NaCl 194, $MgCl_2$ 16, $MgSO_4$ 24, $CaCl_2$ 1, KCl 5, $NaHCO_3$ 0.2, NaBr 0.5, yeast extract 5.

To each medium composed of the above components, predetermined amounts of the saccharide and the furfural compound shown in the table below were added as carbon sources and the culturing was carried out for 72 h.

(Results) The table below shows the 3HV fraction and the weight-average molecular weight, the polydispersity, the dry bacterial weight, and the amount of PHBV produced under each condition.

TABLE 11

|  | Initial glucose concentration (g/L) | Initial Furfural concentration (g/L) | Initial HMF concentration (g/L) | 3HV fraction (%) | Mw (×10$^6$) | Mw/Mn | Dry bacterial weight (g/L) | PHBV (g/L) |
| --- | --- | --- | --- | --- | --- | --- | --- | --- |
| Example 15 | 10 | 0.06 | 0 | 13 | 1.2 | 2.15 | 4.07 | 2.15 |
| Example 16 | 10 | 0.1 | 0 | 12 | 0.46 | 1.95 | 5.56 | 1.95 |
| Example 18 | 10 | 0.2 | 0 | 10.5 | 0.26 | 2.27 | 4.26 | 2.27 |
| Example 19 | 10 | 0.4 | 0 | 17.2 | 0.31 | 2.06 | 1.88 | 2.06 |
| Example 20 | 10 | 1.6 | 0 | n.d | n.d | n.d | 0.274 | n.d |
| Example 21 | 10 | 0 | 0.06 | 13.5 | 3.38 | 1.68 | 3.76 | 1.68 |
| Example 22 | 10 | 0 | 0.1 | 14.6 | 0.69 | 1.8 | 4.58 | 1.8 |
| Example 23 | 10 | 0 | 0.2 | 11.2 | 0.44 | 1.72 | 5.66 | 1.72 |
| Example 24 | 10 | 0 | 0.4 | 11.1 | 0.31 | 1.92 | 4.21 | 1.92 |
| Example 25 | 10 | 0 | 1.6 | n.d | n.d | n.d | 0.33 | n.d |

By changing the concentration of furfural and the concentration of HMF, PHBVs having various molecular weights can be produced and the molecular weight can be controlled. The molecular weight of PHBV produced by the furfural compound such as furfural or HMF is considered to be controlled also when sugars other than glucose is used.

L. Examples 26 to 28 <Preliminary Test>

(Materials and methods) In a 300 mL Erlenmeyer flask, the following components were added so that a total volume of a culture solution was 50 mL, and shaking culture was carried out for 72 h at 37° C. and 200 rpm. The initial pH was adjusted to 7.2.
Ingredients in the medium (g/L):
NH$_4$Cl 2, KH$_2$PO$_4$ 0.0375, FeCl$_3$ 0.005, NaCl 194,
MgCl$_2$ 16, MgSO$_4$ 24, CaCl$_2$ 1, KCl 5, NaHCO$_3$ 0.2, and NaBr 0.5

To a medium composed of the above components, a yeast extract (g/L) and a sugar (glucose 5 g/L ("G": Example 26)), xylose 5 g/L ("X": Example 27) or cellobiose 5 g/L ("C": Example 28), were added and the culturing was carried out for 72 h. *Haloferax mediterranei* NBRC14739 was used as a microorganism.

Figure 1:
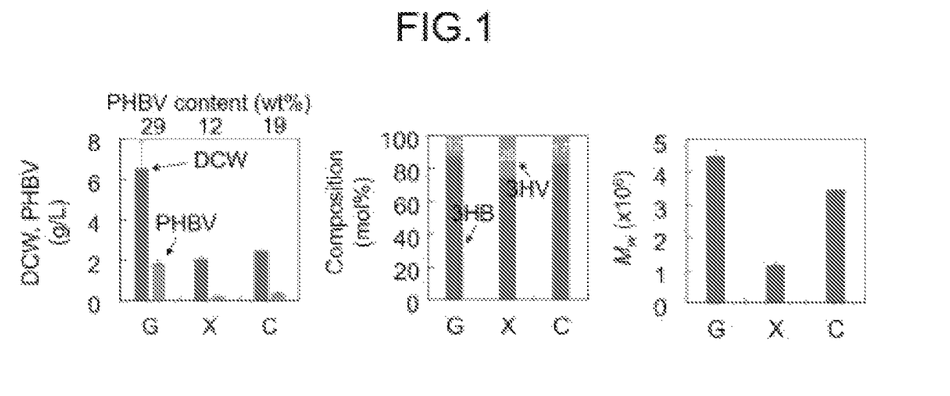
FIG. 1 is a figure showing the amount, the 3HV fraction, and the weight-average molecular weight of PHBV produced in Examples 26 to 28. The notation of "DCW" shown on the vertical axis in the figure on the left indicates a dry bacterial cell concentration.

(Results) FIG. 1 shows the amount of PHBV produced, the 3HV fraction and weight-average molecular weight of PHBV under each condition. The figure clearly shows that, by using only glucose ("G": Example 26), xylose ("X": Example 27) or cellobiose ("C": Example 28), the molecular weight of the obtained PHBV can at least be adjusted between about 4.5 million (when glucose alone was used) and about 1.1 million (xylose alone). Moreover, the 3HV fraction also differed depending on the type of sugars used, and was 12 mol % when glucose alone was used, and it was 25 mol % when xylose alone was used, and 17 mol % when cellobiose alone was used.

M. Examples 29 to 35 and Test Examples
(Production of Cold-Drawn Film and Evaluation of Physical Properties of the Film)

It is known that when molecular chains are oriented in the same direction, a tensile strength is improved with respect to the oriented direction. Molecular chains of the PHA of the present invention were thus oriented by a method referred to as cold drawing (for example, the method described in Patent Document 5), and a degree of improvement in a tensile strength of the PHA of the present invention was measured, from which a comparison was made with respect to the prior art.

Each sample was prepared by cutting a cast film of an ultrahigh molecular weight PHBV (Mw=3.07×10$^6$, Mw/Mn=1.87, a 3HV fraction of 8.4%) into 10 mm×30 mm with a cutter.

The same sample was cold-drawn 10-fold, and then the resulting film was heat-treated (crystallized) at different temperatures and left for longer than 3 days, and a tensile strength thereof was measured. The specific method was as follows:
  (1) each sample was heat-pressed at a temperature of 170° C. or 200° C. (for comparison with the result on the PHB having a higher melting point, described in Non Patent Document 9) and at 3 MPa for 30 seconds to melt completely,
  (2) rapidly cooling the molten film obtained in (1) in ice water to make an amorphous film,
  (3) the amorphous film was oriented by drawing it as it was in ice water to a 10-fold length,
  (4) tension heat treatment was carried out for 2 hours at a temperature of 25° C., 60° C., 80° C., 100° C. or 120° C. for crystallization and
  (5) stored at room temperature for more than 3 days to obtain a cold-drawn film for measurement of a tensile strength.

EZ Test EZ-LX was used to measure the tensile strength. For the measurement, an initial length was 30 mm and a tensile rate was 20 mm/min; the measurement was carried out three times per one condition. The tensile strength before cold drawing was 29.9 MPa.

When carrying out physical property analysis, an absolute molecular weight may be used in a notation of molecular weight. For example, since the absolute molecular weight is used for the notation of molecular weight in Patent Document 5 and Non Patent Document 9, notation of absolute molecular weight is used in the present Examples.

An absolute molecular weight of PHA is known to be calculable according to the following formula:

(Absolute molecular weight)=(PS-equivalent GPC molecular weight)×0.7

The value of the absolute molecular weight calculated by using this calculation formula was also used as a value of the molecular weight in the present Examples.

Figure 2:
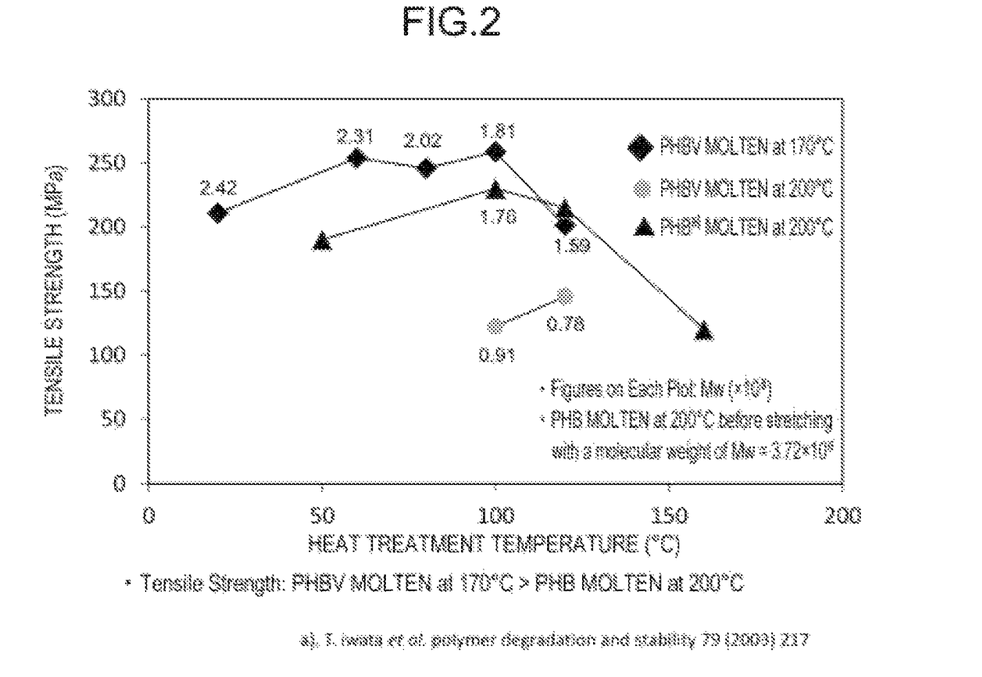
FIG. 2 is a graph illustrating the results of production and evaluation of the physical properties of the films of Examples 29 to 35 and Test Example for films uniaxially cold-drawn 10-fold. The corresponding numerical values disclosed in Non Patent Document 9 are also plotted (▲). The molecular weight described in the present examples is an absolute molecular weight.

The results are shown in the table below and FIG. 2.

TABLE 12

| Sample No. | Example No. | (1) Melting temperature (° C.) | (4) Heat treatment temperature (° C.) | Sample thickness (μm) | Sample width (mm) | Tensile strength (MPa) |
|---|---|---|---|---|---|---|
| 1 | 29 | 170 | 25 | 102.9 ± 1.9 | 3.71 ± 0.14 | 210.9 ± 21.0 |
| 2 | 30 | 170 | 60 | 88.6 ± 0.6 | 3.13 ± 0.18 | 253.7 ± 40.2 |
| 3 | 31 | 170 | 80 | 87.7 ± 0.2 | 3.13 ± 0.07 | 245.9 ± 29.6 |
| 4 | 32 | 170 | 100 | 83.0 ± 0.2 | 2.43 ± 0.03 | 258.7 ± 26.0 |
| 5 | 33 | 170 | 120 | 93.0 ± 0.2 | 3.04 ± 0.11 | 201.2 ± 18.6 |
| 6 | 34 | 200 | 100 | 114.9 ± 3.3 | 3.88 ± 0.08 | 122.3 ± 12.9 |
| 7 | 35 | 200 | 120 | 99.0 ± 1.0 | 3.50 ± 0.01 | 145.5 ± 3.8 |

The maximum tensile strength when cold-drawn 10-fold reached 258.7 MPa (Example 32). This tensile strength exceeded the tensile strength of the known ultrahigh molecular weight PHB cold-drawn 10-fold described in Non Patent Document 9 at least in the case of the heat treatment temperature of 50° C. to 100° C. (FIG. 2) also exceeding by about 10% the maximum value of the strength at break of the film (237 MPa) (Example 8 in Patent Document 5), which was obtained by cold-drawing 10-fold the ultrahigh molecular weight PHB described in Non Patent Document 9 and Patent Document 5 (the description thereof is partially overlapping that of Non Patent Document 9).

Furthermore, Non Patent Document 10 discloses data on the case where the same treatment (10-fold cold drawing) was carried out for a normal molecular weight PHBV (Mw=1.0×10$^6$), which data show that the tensile strength in the case of drawing 10-fold and heat treating for 2 h at 75° C. was 117 MPa. On the other hand, the tensile strengths in the present test were 253.7 MPa and 245.9 MPa when the heat treatment was carried out for 2 hours at a temperature in the vicinity of 75° C. (60° C. and 80° C.), which temperature was the heat treatment temperature described in Non Patent Document 10. Namely, the PHBV of the present invention, due to the ultrahigh molecular weight, has achieved a higher tensile strength by more than 100% than that of the prior art.

From these results and findings, the cold-drawn film of the copolymer of the present invention, wherein 3-hydroxybutanoic acid and 3-hydroxyvaleric acid is randomly copolymerized, clearly has the excellent tensile strength. Moreover, the ultrahigh molecular weight of the PHA of the present invention clearly achieves an effect of improving the tensile strength.

INDUSTRIAL APPLICABILITY

With the present invention, the PHA can be produced under control of the weight-average molecular weight between, for example, 200,000 to 6 million. The present invention hence greatly contributes to the development of the PHA manufacturing industry and related industries.

The invention claimed is:

1. A random copolymer of 3-hydroxybutanoic acid and 3-hydroxyvaleric acid having a weight average molecular weight ranging from 5 million to 6 million g/mol.

2. The random copolymer according to claim 1, wherein the ratio of the number of moles of 3-hydroxyvaleric acid to the total number of moles of 3-hydroxybutanoic acid and 3-hydroxyvaleric acid (the 3HV fraction) of the random copolymer is 5.0% to 40.0%.

3. A method for producing a random copolymer of 3-hydroxybutanoic acid and 3-hydroxyvaleric acid having a weight average molecular weight of between 5 million to 6 million g/mol, comprising culturing *Haloferax mediterranei* to obtain polyhydroxyalkanoic acid as a culture product,
   wherein the culture comprises a carbon source comprising a sugar,
   wherein the sugar is selected from the group consisting of:
   (a) glucose;
   (b) glucose as well as one or more of xylose, cellobiose, glucuronic acid, arabinose, mannose, galactose, and sucrose; and
   (c) one or more of xylose, cellobiose, glucuronic acid, arabinose, mannose, galactose, and sucrose.

4. The method according to claim 3, wherein one or more of xylose, cellobiose, glucuronic acid, arabinose, mannose, galactose, and sucrose in (b) or (c) are xylose or cellobiose or xylose and cellobiose.

5. A method of culturing *Haloferax mediterranei* and controlling the weight average molecular weight of a random copolymer of 3-hydroxybutanoic acid and 3-hydroxyvaleric acid obtained as a culture product,
   wherein the culture comprises a carbon source comprising a sugar,
   wherein the sugar is selected from the group consisting of:
   (a) glucose;
   (b) glucose as well as one or more of xylose, cellobiose, glucuronic acid, arabinose, mannose, galactose, and sucrose; and
   (c) one or more of xylose, cellobiose, glucuronic acid, arabinose, mannose, galactose, and sucrose,
   wherein the weight average molecular weight of the random copolymer of 3-hydroxybutanoic acid and 3-hydroxyvaleric acid is between 5 million and 6 million g/mol.

6. A method for producing a random copolymer of 3-hydroxybutanoic acid and 3-hydroxyvaleric acid having a weight average molecular weight of between 5 million to 6 million g/mol comprising culturing *Haloferax mediterranei* to obtain the random copolymer of 3-hydroxybutanoic acid and 3-hydroxyvaleric acid as a culture product,
   wherein the culture comprises a carbon source comprising a sugar and a furfural compound,
   wherein the sugar is selected from the group consisting of:
   (a) glucose;
   (b) glucose as well as one or more of xylose, cellobiose, glucuronic acid, arabinose, mannose, galactose, and sucrose; and
   (c) one or more of xylose, cellobiose, glucuronic acid, arabinose, mannose, galactose, and sucrose.

7. A method of culturing *Haloferax mediterranei* and controlling a molecular weight of a random copolymer of 3-hydroxybutanoic acid and 3-hydroxyvaleric acid obtained as a culture product,
   wherein the culture comprises a carbon source comprising a sugar and a furfural compound, wherein the sugar is selected from the group consisting of:
 (a) glucose;
 (b) one or more of glucose and xylose, cellobiose, glucuronic acid, arabinose, mannose, galactose, and sucrose; and
 (c) one or more of xylose, cellobiose, glucuronic acid, arabinose, mannose, galactose, and sucrose,
wherein the weight average molecular weight of the random copolymer of 3-hydroxybutanoic acid and 3-hydroxyvaleric acid is between 5 million and 6 million g/mol.

8. A cold-drawn film comprising a random copolymer of 3-hydroxybutanoic acid and 3-hydroxyvaleric acid having a weight average molecular weight of between 5 million to 6 million g/mol.

9. A method of making the cold-drawn film according to claim 8 comprising the following steps:
 (1) melting a random copolymer of 3-hydroxybutanoic acid and 3-hydroxyvaleric acid to obtain a molten film;
 (2) rapidly cooling the molten film obtained in (1) in ice water to make an amorphous film;
 (3) drawing the amorphous film obtained in (2) in ice water to increase the length of the amorphous film 10-fold and to orient the amorphous film; and
 (4) subjecting the oriented amorphous film obtained in (3) to tension heat treatment to obtain a crystallized cold-drawn film.

10. The cold-drawn film according to claim 8, wherein the ratio of the number of moles of 3-hydroxyvaleric acid to the total number of moles of 3-hydroxybutanoic acid and 3-hydroxyvaleric acid (the 3HV fraction) in the random copolymer is 5% to 15%.

\* \* \* \* \*

UNITED STATES PATENT AND TRADEMARK OFFICE
CERTIFICATE OF CORRECTION

| | | |
|---|---|---|
| PATENT NO. | : 12,173,347 B2 | Page 1 of 1 |
| APPLICATION NO. | : 17/276965 | |
| DATED | : December 24, 2024 | |
| INVENTOR(S) | : Kotaro Ino et al. | |

It is certified that error appears in the above-identified patent and that said Letters Patent is hereby corrected as shown below:

On the Title Page

Item "(71) Applicant:" replace:
"SUMITMO FORESTRY CO., LTD."
With:
--SUMITOMO FORESTRY CO., LTD.--

Signed and Sealed this
Eleventh Day of November, 2025

John A. Squires
*Director of the United States Patent and Trademark Office*